United States Patent [19]

Hansen et al.

[11] 4,181,669
[45] Jan. 1, 1980

[54] STEROID ESTERS PREPARATION

[75] Inventors: Bertil Hansen, Helsingborg; Krister Holmberg, Mölndal, both of Sweden

[73] Assignee: Aktiebolaget Leo, Sweden

[21] Appl. No.: 863,057

[22] Filed: Dec. 21, 1977

[30] Foreign Application Priority Data

Dec. 31, 1976 [GB] United Kingdom ............... 54544/76

[51] Int. Cl.$^2$ ........................... C07J 71/00; C07J 5/00
[52] U.S. Cl. ............................ 260/397.4; 260/397.45; 260/397.47; 260/397.5; 260/397.2; 260/239.55 D

[58] Field of Search ..................... 260/397.45, 397.47, 260/239.55 D, 397.4

[56] References Cited

U.S. PATENT DOCUMENTS 4,082,747  4/1978  Chen .................. 260/239.57

Primary Examiner—Elbert L. Roberts
Attorney, Agent, or Firm—Gordon W. Hueschen

[57] ABSTRACT

This invention relates to an improved steroid ester synthesis in which a carbodiimide, in combination with an acid catalyst, is used as condensing agent.

25 Claims, No Drawings

STEROID ESTERS PREPARATION

This invention relates to an improved steroid ester synthesis in which a carbodiimide, in combination with an acid catalyst, is used as condensing agent for the reaction between the steroid alcohol and the esterifying agent.

BACKGROUND OF THE INVENTION

There are numerous procedures available for the preparation of carboxylic esters from acid and hydroxyl components. However, the methods generally involve activation of either the acid (e.g. in the form of acyl halide) or the hydroxyl (e.g. as ester) component, which means introduction of an extra reaction step.

In the following, references to the literature are given by numbers within brackets. The numbers refer to literature sources listed after the examples.

During recent years carbodiimides, and especially N,N¹-dicyclohexylcarbodiimide (in the following abbreviated as DCC), have attracted increasing attention as condensing agents in ester synthesis (1, 2). Since both the acid and the hydroxyl compound are used as such in the reaction this synthesis has the obvious advantage of proceeding without the extra activation step of at least one reactant.

Esters of carboxylic acids with primary or secondary alcohols, as well as with phenols, are obtainable with this method (3). Tertiary alcohols generally react in only very low yield (3). However, the yield of ester is usually decreased by the simultaneous formation of an N-acylurea derivative as by-product, as illustrated below (4, 5).

$$R^1-COOH + R^3-N=C=N-R^4 \longrightarrow$$

$$\begin{array}{c} R^3-NH-CO-N-R^4 \\ | \\ CO-R^1 \end{array}$$
N-acylurea derivative This by-product may also cause problems in the work-up procedure and contaminate the desired ester. Numerous attempts have been made to increase the yield of ester by choosing reaction conditions so as to avoid the formation of the by-product. It has been found that the use of pyridine as solvent promotes the formation of ester (1, 6), although the appearance of smaller or larger quantities of N-acylurea usually cannot be avoided.

It has now, surprisingly, been found that addition of a strong acid to the pyridine solution considerably increases the yield of ester and decreases, or even prevents, the formation of the N-acylurea compound, and that the strong acid can be used in a catalytic amount. Table 1 shows that condensation of carboxylic acids with phenol and primary and secondary alcohols in pyridine with DCC in the presence of a catalytic amount of p-toluenesulfonic acid (in the following abbreviated as pTSA) gives excellent yields of ester, whereas reaction without said catalyst gives a much poorer result, due to the formation of the corresponding N-acylurea derivative.

As is seen in Table 1, the yield of ester is not particularly outstanding when tertiary alcohols are employed, even with pTSA added to the reaction mixture. However, the promoting effect of the acid catalyst on the ester formation is definitely evident even in this case.

Although the exact mechanism involved in the reaction is not fully understood, the fact that increased yields and purity of desired carboxylic acid esters are realized by the addition of the strong acid into the basic reaction mixture is indeed unexpected as, in fact, the addition of strong acid into the present basic esterification reaction mixture is not indicated by any known prior art for any purpose. In theory, the desirable result occurs due to suppression of side reactions, which is most likely due in some way or other to the presence of a salt between the pyridine and the strong acid, although once again the way in which this salt operates to suppress the undesired side reactions is not presently clear.

As is seen from Table 1, carboxylic esters are obtained in high yields from phenols and from primary and secondary alcohols when approximately

Table 1

Reaction of a carboxylic acid, a hydroxyl compound, and DCC
(molar ratio 1.0: 1.1: 1.2) in pyridine.
(See examples 1 and 2 for experimental details.)

a) ⌬—COOH + R—OH $\xrightarrow{DCC}$ ⌬—COO—R

| R | yield (%)+ with pTSA | without pTSA |
|---|---|---|
| n-hexyl | 95 | 40 |
| i-propyl | 98 | 5 |
| t-butyl | 8 | 0 |
| phenyl | 96 | 20 | b) 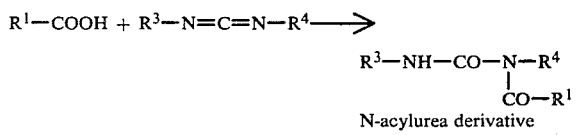

⌬—CH₂CH₂COO—R²

| R² | yield (%)+ with pTSA | without pTSA |
|---|---|---|
| n-butyl | 96 | 66 |
| i-propyl | 99 | 58 |
| t-butyl | 17 | 3 |
| phenyl | 93 | 39 |

+Several esterifications of benzoic acid using DCC as condensing agent are mentioned in the literature. Without any catalyst present methyl benzoate has been prepared in a 60% yield using a large excess of methanol (4), and phenyl benzoate has been obtained in a 12% yield from equimolar amounts of reactants (7).

TABLE 2

Yield of steroid esters of carboxylic acids.
(See Examples 3, 4, and 5 for experimental details.)

| ester | yield (%)+ with pTSA | yield (%)+ without pTSA |
|---|---|---|
| [steroid ester with CH₂O—C(=O)—(CH₂)₃—C₆H₄—N(CH₂CH₂Cl)₂ side chain, C=O and —OH groups, HO and O substituents on steroid] | 85 | 74 |
| [steroid ester with O—C(=O)—(CH₂)₂—C₆H₄—O(CH₂)₅CH₃ side chain, O substituent on steroid] | 87 | 50 |
| [steroid ester with CH₂O—C(=O)—C₆H₃(N(CH₂CH₂Cl)₂)(CH₃) side chain, C=O and —OH groups, HO and O substituents on steroid] | 89 | 73 |

+Calculated as pure compound equimolar amounts of the reacting carboxylic acid and hydroxyl compound are employed. Although the present invention is of general value for the preparation of esters, its main area of application will therefore be in the synthesis of esters of expensive starting materials, where the use of large excess of one reactant is highly uneconomical.

Steroid alcohols esterified with valuable carboxylic acids are one such type of esters which are preferably synthesized by the method of the present invention. This class of esters is of great pharmaceutical interest, e.g. as anticancer agents (14, 16) and as long-acting hormonal agents (15). Several steroid esters of carboxylic acids have now been prepared by pyridine using DCC as condensing agent. The catalytic effect of pTSA on the reactions is evident from the yields given in Table 2.

Other types of esters of great pharmaceutical interest which are prepared from expensive starting materials, and which may conveniently be synthesized by the method of the present invention, are for instance esters of penicillins, cephalosporins, prostaglandins, neuroleptics, and certain amino acids.

In the esterifications mentioned above, pTSA and DCC may be replaced by other strong acids and carbodiimides, respectively. Thus, the promoting effect on the formation of ester exerted by an acid catalyst in the presence of pyridine seems to be a general phenomenon when carbodiimides are used as condensing agents.

SUMMARY OF THE INVENTION

The object of the invention is to provide a process for the preparation of carboxylic esters of high purity and at an improved yield. The process comprises reacting in solution a carboxylic acid, a hydroxyl compound, and a carbodiimide in the presence of pyridine, or pyridine substituted in 3- or 4-position with a lower alkyl group, and a strong acid which can be present in a catalytic amount, the improvement being characterized by the use of said strong acid.

Carboxylic acids suitable to be transferred to their carboxylic acid esters by using the method of the present invention may have very different structures but are in general expensive to buy or prepare. If such acids have substituents which may react with the carboxylic acid part of the molecule during the reaction conditions employed, e.g. reactive hydroxy-, amino-, or thiol-groups, such groups are protected by methods known per se during the reaction (see for example ref. 17).

Among carboxylic acids of interest the following general types may be mentioned: substituted benzoic acids, substituted arylalkanoic acids, e.g. substituted phenylalkanoic acids, and saturated or unsaturated, straight or branched alkanoic acids, optionally substituted, and having at most 22 carbon atoms, e.g. decanoic acid, undecylenic acid, arachidonic acid, behenic acid, and 2-ketobutyric acid.

Other types of carboxylic acids are such as: substituted or unsubstituted prostanoic acids and its homologs, e.g. the natural or synthetic prostaglandins; N-derivatives of 6-aminopenicillanic acid and 7-aminocephalosporanic acid such as benzylpenicillin, phenoxymethylpenicillin, dicloxacillin, cephalothin, and cephapirin; amino acids; peptides; different kinds of glucuronides, ethacrynic acid, dehydrocholic acid, 1-adamantanecarboxylic acid, furosemide, and retinoic acid.

Preferred carboxylic acids are substituted benzoic acids and substituted phenylalkanoic acids, both types having at most 22 carbon atoms and in either case having a bis β- or α-haloalkyl substituted amino group or an alkoxy group having preferably three to twelve carbon atoms, as one substituent in the benzene ring. Especially preferred acids of these types are: 3-(bis-(2-chloroethyl)amino)-4-methylbenzoic acid, 4-(bis-(2-chloroethyl)amino)phenylacetic acid, 3-(4-bis-(2-chloroethyl)

aminophenyl)-2-aminopropionic acid, 3-(4-bis-(2-chloroethyl)aminophenyl)-2-acetamidopropionic acid, 4-(4-bis-(2-chloroethyl)aminophenyl)butyric acid, and 3-(4-alkoxyphenyl) propionic acids such as 3-(4-propyloxyphenyl)propionic acid and 3-(4-hexyloxyphenyl) propionic acid.

Hydroxy group containing compounds suitable to be esterified by carboxylic acids using the method of the present invention may have very different structures but are in general expensive to buy or prepare. It is preferred that hydroxyl groups which are to be esterified are primarily, secondary, or phenolic. If the hydroxy compounds have additional substituents which may react, during the reaction condition employed, such substituents, such as carboxylic acid groups, hydroxy groups, thiol groups, or amino groups, are protected by methods known per se during the reaction (see for example ref. 17 and 18).

Among suitable compounds containing hydroxy groups the following general types may be mentioned: natural or synthetic steroids having a cyclopentanophenanthrene carbon-carbon skeleton or its homologs and containing up to a maximum of 40 carbon atoms and having at least one primary, secondary, or phenolic hydroxy group as a substituent; saturated or unsaturated alkanols, optionally substituted; e.g. 2-octanol, 9-decen-1-ol, and 1-octyn-3-ol; tetracyclines; neuroleptics, e.g. flupenthixol, acephenazin, and clopenthixol.

Other types of hydroxy compounds are such as: morphine, nalorphine, oxyphenylbutazone, vitamins A and D, erythromycin, chloramphenicol, atropine, podophyllotoxin, yohimbine, adamantanols, cytochalosin B, quinidine, and 4-(bis(2-chloroethyl)amino)phenol.

Preferred hydroxy group containing compounds are steroids having a carbon-carbon skeleton selected from the group consisting of: estra-1,3,5(10)-triene, androstane, androst-4-ene, androst-5-ene, estr-4-ene, estr-5(10)-ene, pregn-4-ene, pregna-4,6-diene, pregn-5-ene, pregna-1,4-diene, cholestane, and cholest-5-ene.

It is preferred that the hydroxy group or groups which are to be esterified are situated in the 3-, 16-, 17-, or 21-positions of the said carbon-carbon skeletons. Their 17- and 21-positions are especially preferred when the hydroxy group to be esterified is a secondary one or a primary one, respectively.

Preferred steroids have a nucleus selected from the group consisting of: estra-1,3,5(10)-trien-3-ol-17-ones, estra-1,3,5(10)-triene-3,16-diol-17-ones, estra-1,3,5(10)-triene-3,16,17-triols, estra-1,3,5(10)-triene-3,17-diols, androstan-3-ol-17-ones, androstan-17-ol-3-ones, androstane-3,17-diols, androst-4-en-17-ol-3-ones, androst-4-ene-3,17-diols, androst-5-en-3-ol-17-ones, androst-5-en-17-ol-3-ones, androst-5-ene-3,17-diols, estr-4-en-17-ol-3-ones, estr-4-ene-3,17-diols, pregna-4-en-21-ol-3,20-diones, pregn-4-ene-11,21-diol-3,20-diones, pregn-4-ene-21-diol-3,11,20-triones, pregn-4-ene-17,21-diol-3,11,20-triones, pregn-4-ene-11,17,21-triol-3,20-diones, pregn-4-ene-11,16,17,21-tetraol-3,20-diones, pregna-1,4-diene-17,21-diol-3,11,20-triones, pregna-1,4-diene-11,17,21-triol-3,20-diones, pregna-1,4-diene-11,16,17,21-tetraol-3,20-diones, cholestan-3-ols, and cholest-5-en-3-ols wherein any further substitution in the carbon-carbon skeleton of said steroid nucleus is at most a tri-substitution wherein the positions of the steroid carbon-carbon skeleton which are substituted are selected from the positions consisting of the 6-, 9-, 17-, and 18-positions; where the substitution, if any, comprises at least one substituent selected from the group consisting of methyl, ethynyl, fluoro, and chloro.

Hydroxy groups present in said steroid nucleus and which are not to be esterified by the present method may be free, esterified with a monocarboxylic acid selected from the group consisting of lower alkanoic acids and benzoic acid, etherified with an alcohol selected from the group consisting of aliphatic or alicyclic alcohols having at most 6 carbon atoms, or transformed to an acetonide.

As examples of steroids and derivatives thereof which can be used as hydroxyl compounds in the present method the following may be mentioned using the trivial names of the steroid as found in the literature (e.g. in the ninth edition of the Merck Index):

estrone; estradiol; estradiol 3-acetate; estradiol 17$\beta$-acetate; estriol 3-acetate; estriol 3,16$\alpha$-diacetate; estriol 16$\alpha$,17$\beta$-diacetate; estradiol 3-methylether; estradiol 3-cyclopentylether; 17$\alpha$-ethynylestradiol; androsterone; epiandrosterone; dihydrotestosterone; androstanediol; androstanediol 3$\alpha$-acetate; testosterone; androstenediol; androstenediol 3$\beta$-acetate; dehydroepiandrosterone; 19-nortestosterone; ethynodiol; pregnenolone; desoxycorticosterone; cortisone; hydrocortisone; prednisone; prednisolone; prednisolone 17-benzoate; 9$\alpha$-fluoro-16$\alpha$-methylprednisolone; 9$\alpha$-fluoro-16$\beta$-methylprednisolone; 9$\alpha$-fluoro-16$\alpha$-hydroxyprednisolone, 16,17-acetonide; and cholesterol.

Especially preferred steroids are testosterone, dihydrotestosterone, 19-nortestosterone, deoxycorticosterone, cortisone, hydrocortisone, prednisone, and prednisolone.

Most preferred are 19-nortestosterone and prednisolone.

Various types of carbodiimides may be employed such as N,N$^1$-aliphatic, e.g. N,N$^1$-dicyclohexylcarbodiimide and N,N$^1$-diisopropylcarbodiimide, or N,N$^1$-aromatic, e.g. N,N$^1$-di-p-tolylcarbodiimide.

The preferred carbodiimide is N,N$^1$-dicyclohexylcarbodiimide.

The strong acid may be an organic or an inorganic acid, such as a sulfonic acid, e.g. p-toluenesulfonic acid or methanesulfonic acid, sulfuric acid, nitric acid, perchloric acid, or a hydrogen halide, e.g. hydrogen chloride, hydrogen bromide, or hydrogen iodide. According to usual definition, as recognized in the chemical art, such strong acid has a thermodynamic dissociation constant K in water at 25° C. greater than one (K being defined in ref. 19). Examples of dissociation constants for some of these acids are as follows: nitric acid has a K of 23 and methanesulfonic acid has a K of about 4 (see ref. 22).

The sulfonic acids are preferred.

The strong acid may be used in a catalytic amount, preferably in the range of 0.02 to 0.10 mole per mole of limiting reactant as large amounts may lead to side-reactions. In this disclosure the limiting reactant means the least abundant ester forming component calculated on a molar basis.

The solvent employed may be any conventional solvent, well known in the art for esterification reactions, or mixture of such solvents compatible with the reaction. Such solvent may be hydrocarbons, halogenated hydrocarbons, ethers, esters or ketones.

Among the halogenated and non-halogenated hydrocarbons the following may be mentioned as representative solvents: chloroform, dichloromethane, benzene, chlorobenzene, and toluene.

It is preferred that the ethers, esters, and ketones are aliphatic. Representative examples of such solvents are dioxane, tetrahydrofurane, diethyl ether, ethyl acetate, and acetone.

As indicated above, the presence of pyridine, or pyridine substituted in 3- or 4-position with a lower alkyl group, is essential to the reaction. The pyridine, or the above-mentioned pyridine derivative, is preferably used in an amount at least equivalent to the limiting reactant and may be used even as the sole solvent.

Whenever convenient, any of the reactants may be used as solvent.

Pyridine is the particularly preferred solvent.

REACTION TEMPERATURE

The reaction may be conducted conveniently at room temperature. The reaction is frequently exothermic and can be controlled by a cooling process if desired.

The temperature is not critical except that it should not be so high as to produce undesirable side-effects, or so low that the reaction proceeds so slowly as to be at an uneconomic rate.

REACTION PRESSURE

The pressure used above the reaction mixture during the reaction is not particularly critical. For most purposes atmospheric pressure is adequate. In some cases, however, superatmospheric pressure may be desired and is serviceable. The pressure may also be below atmospheric pressure, if desired.

REACTION TIME

The reaction period may vary widely but for best yields and greatest economy the reaction must be allowed sufficient time to go to completion. Usually, at room temperature, 24 hours reaction time is sufficient.

MOLAR RATIOS

The ester forming components, namely the alcohol and the carboxylic acid are generally employed in approximately equivalent amounts, However, excess of one reactant does not give rise to any detrimental effects whatever upon the reaction except loss of economy and the usually attendant problems of incompletely reacted starting materials. When esters of lower alkanols are being made, the alkanols are sometimes employed as cosolvent in the reaction, and the excess is subsequently removed by distillation.

A slight molar excess of carbodiimide over the molar amount of the carboxylic groups is usually employed. Unreacted carbodiimide may subsequently be destroyed by the addition of a lower alkanoic acid, e.g. acetic acid.

WORK-UP PROCEDURE

The reaction mixture containing the desired product is worked up according to normal procedures, as apparent to those skilled in the art.

In this disclosure the expression "lower" means that the group referred to contains one to four carbon atoms, inclusive. Thus, lower alkyl, lower alkanol, and lower alkanoic include: methyl, ethyl, propyl, isopropyl, butyl, isobutyl, secondary butyl, tertiary butyl, methanol, ethanol, propanol, isopropanol, butanol, isobutanol, secondary butanol, tertiary butanol, methanoic, ethanoic, propanoic, butanoic, and isobutanoic.

The nomenclature used in this disclosure is in accordance with the rules issued by the IUPAC Commission on the Nomenclature of Organic Chemistry, 1957, 1965, and 1971.

The following examples are intended to illustrate but not to limit the scope of the invention, although the reagents named and the esters obtained are of particular interest for our intended purposes.

EXAMPLE 1 pTSA (0.100 g) is added to a mixture of benzoic acid (12.2 g) and 1-hexanol (11.2 g) in pyridine (30 ml). To the homogenous solution DCC (24.8 g) is added, and the solution is stirred at room temperature for 24 h. After addition of acetic acid (10 ml) the solution is kept overnight at +4° C. and then filtered. The crystals are washed with cold pyridine, and to the filtrate chloroform (100 ml) and ice (100 g) are added. The stirred mixture is acidified with 5 M HCl, and phases are separated, and the organic phase washed with water, aq. NaHCO$_3$, and water, dried and evaporated to give hexyl benzoate (95% yield) b. p. 99°–100° C. (0.10 mm Hg) [lit. (10), 101° C. (0.10 mm Hg)].

When the above reaction is carried out in the absence of pTSA, the yield of ester is reduced to 40%.

When 1-hexanol is replaced by equimolar amounts of isopropanol in the above reaction, the yield of isopropyl benzoate is 98% when the reaction is carried out in the presence of pTSA and 5% when the reaction is performed in the absence of pTSA. B. p. of isopropyl benzoate: 104°–105° C. (20 mm Hg) [lit. (11), 106.5°–107.5° C. (21 mm Hg)].

When 1-hexanol is replaced by equimolar amounts of tert. butanol in the above reaction, tert. butyl benzoate is obtained in 8% yield after chromatography of the reaction product on a silica gel column if the reaction is carried out in the presence of pTSA. If pTSA is omitted, no tert. butyl benzoate is obtained from the reaction mixture. B. p. of tert. butyl benzoate: 94°–95° C. (10 mm Hg) [lit. (11), 91.3° C. (7.5 mm Hg)].

When 1-hexanol is replaced by equimolar amounts of phenol in the above reaction, phenyl benzoate is obtained in a 96% yield if the reaction is carried out in the presence of pTSA and in a 20% yield if the reaction is performed in the absence of pTSA. M. p. of phenyl benzoate after recrystallization from petroleum ether: 69°–70° C. (lit. (7), 70°–71° C.).

EXAMPLE 2

To a mixture of 3-phenylpropionic acid (15.0 g) and 1-butanol (8.15 g) in pyridine (30 ml) pTSA (0.100 g) is added. When the solution is homogeneous, DCC (24.8 g) is added, and the solution is stirred at room temperature for 24 h. After addition of acetic acid (10 ml) the reaction mixture is worked up as in Example 1. A 96% yield of butyl 3-phenylpropionate is obtained, b. p. 112°–3° C. (1 mm Hg) [lit. (12), 91° C. (0.3 mm Hg)].

When pTSA is omitted from the above reaction mixture the yield of ester is reduced to 66%.

Substituting N,N$^1$-diisopropylcarbodiimide, N-(3-dimethylaminopropyl)-N$^1$-ethylcarbodiimide, or N,N$^1$-di-p-tolylcarbodiimide for DCC in the above reaction leads to yields of 93, 88, and 90%, respectively, in the presence of pTSA, and to yields of 58, 69, and 66%, respectively, in the absence of pTSA.

Replacing 1-butanol by equimolar amounts of isopropanol in the first reaction in this example gives a 99% yield of isopropyl 3-phenylpropionate if the reaction is carried out in the presence of pTSA and a 58% yield of said ester if the reaction is performed in the absence of pTSA. B. p. of isopropyl 3-phenylpropionate: 92°–3° C. (1 mm Hg) [lit. (12), 89° C. (0.9 mm Hg)].

Replacing 1-butanol by equimolar amounts of tert. butanol in the first reaction in this example gives a 17% yield of tert. butyl 3-phenylpropionate if the reaction is carried out in the presence of pTSA and a 3% yield of said ester if the reaction is performed in the absence of pTSA. B. p. of tert. butyl 3-phenylpropionate: 95°–6° C. (1 mm Hg) [lit. (12), 84°–5° C. (0.5 mm Hg)].

When 1-butanol is replaced by equimolar amounts of phenol in the first reaction in this example, phenyl 3-phenylpropionate is obtained in a 93% yield if the reaction is performed in the presence of pTSA and in a 39% yield if the reaction is carried out in the presence of pTSA. M. p. of phenyl 3-phenylpropionate after distillation at reduced pressure and recrystallization from light petroleum: 15°–16° C. (lit. (13), 16°–17° C.).

EXAMPLE 3

11β,17,21-trihydroxypregna-1,4-diene-3,20-dione (prednisolone, 7.20 g) and 4-[4-(N,N-bis(2-chloroethyl)amino)phenyl]butyric acid (chlorambucil, 7.00 g) is dissolved in dry pyridine (60 ml). pTSA (0.200 g) is added and the mixture is stirred for 15 min. To the homogeneous solution DCC (5.77 g) is added, and stirring is continued for 24 h at room temperature. Acetic acid (2 ml) is added, and the reaction mixture is kept overnight at +4° C. The solution is filtered and the crystals are washed with cold pyridine. To the filtrate a mixture of ethyl acetate (100 ml), ether (100 ml), and ice (100 g) is added, and 5 M HCl is then slowly added to the stirred solution until pH reaches 2.5. The organic phase is washed with water, 0.5 M aq. $K_2CO_3$, and water. After removal of the solvent and recrystallization from isopropanol 21-[4-(4-(N,N-bis(2-chloroethyl)amino)phenyl)butanoyloxy]-11β,17-dihydroxypregna-1,4-diene-3,20-dione (prednimustine), m. p. 165°–166° C., is obtained in an 85% yield.

The structure is confirmed by comparison with a sample prepared by another route (14) and by physical data such as NMR, IR, and analysis for Cl and N. The significant signals of the NMR spectrum (60 MHz, CDCl$_3$) are the following: δ(ppm) 0.95 (s, 3H, H-18), 1.44 (s, 3H, H-19), 3.67 (s, 8H, —CH$_2$CH$_2$Cl), 4.50 (broad signal, 1H, H-11), 5.00 (s, 2H, —COCH$_2$OCO—), 6.03 (d, 1H, H-4, $J_{4,2}=2$ Hz), 6.30 (dd, 1H, H-2, $J_{2,1}=10$ Hz, $J_{2,4}=2$ Hz), 6.69 and 7.12 (doublets, 2H each, aromatic H, J=8 Hz), 7.33 (d, 1H, H-1, $J_{1,2}=10$ Hz).

When the above reaction is carried out in the absence of pTSA the yield of the steroid ester is reduced to 74%.

EXAMPLE 4

Using the same procedure as in Example 3, but replacing chlorambucil with 3-[N,N-bis(2-chloroethyl)amino]-4-methylbenzoic acid, results in a crude product obtained after the evaporation of the ether/ethyl acetate containing <0.5% prednisolone and 2–3% of other impurities when pTSA is present during the reaction and >4% of prednisolone and >10% of other impurities when no pTSA is added to the reaction mixture. After recrystallization from methanol/water the former product gives 21-[3-(N,N-bis(2-chloroethyl)amino)-4-methylbenzoyloxy]-11α,17-dihydroxypregna-1,4-diene-3,20-dione in 89% yield with 0.1% prednisolone being the main impurity and having the m. p. 168° C., while the other crude product gives a product, m. p. 145°–55° C., containing the mentioned compound in 73% yield and 15% of prednisolone and other impurities.

The structure is confirmed by comparison with a sample prepared by another route (14) and by physical data such as NMR, IR, and analysis for Cl and N. The significant signals of the NMR spectrum (60 MHz, CDCl$_3$) are the following: δ(ppm) 0.98 (s, 3H, H-18), 1.44 (s, 3H, H-19), 3.44 (s, 8H, —CH$_2$CH$_2$Cl), 4.50 (broad signal, 1H, H-11), 5.25 (s, 2H, —COCH$_2$OCO—), 6.02 (d, 1H, H-4, $J_{4,2}=2$ Hz), 6.28 (dd, 1H, H-2, $J_{2,1}=10$ Hz, $J_{2,4}=2$ Hz), 7.26 and 7.76 (doublets with J=8 Hz, 1H each, aromatic H), 7.33 (d, 1H, H-1, $J_{1,2}=10$ Hz), 7.85 (s, 1H, aromatic H).

When the above reaction is performed without pTSA the yield of the steroid ester is 73%.

EXAMPLE 5

To a solution of 17β-hydroxyestr-4-en-3-one (5.48 g) and 3-(4-hexyloxyphenyl)propionic acid (5.75 g) in dry pyridine (60 ml) pTSA (0.200 g) and DCC (5.77 g) are added. After 72 h stirring at room temperature acetic acid (2 ml) is added, and the reaction mixture is kept overnight at +4° C. The same work-up procedure as in Example 1 gives 17β-[3-(4-hexyloxyphenyl)propanoyloxy]estr-4-en-3-one (m. p. 52°–53° C.) in a 87% yield after recrystallization from methanol/water.

The structure is confirmed by comparison with a sample prepared by another route (15) and by physical data such as NMR, IR, and UV. The significant signals of the NMR spectrum (60 MHz, CDCl$_3$) are the following: δ(ppm), 0.80 (s, 3H, H-18), 3.93 (t, 2H, φ-O-CH$_2$-), 4.65 (t, 1H, H-17), 5.85 (s, 1H, H-4), 6.83 and 7.11 (doublets, 2H, each, aromatic H, J=9 Hz).

When the above reaction is carried out in the absence of pTSA the yield of the steroid ester is reduced to 50%.

EXAMPLE 6 pTSA (0.100 g) is added to a mixture of benzoic acid (12.2 g) and isopropanol (6.61 g) in ethyl acetate-pyridine 9:1 (100 ml). After 15 min. stirring, DCC (24.8 g) is added and stirring is continued at room temperature for 24 h. Acetid acid (10 ml) is added, and the reaction mixture is worked-up as described in Example 1 to give isopropyl benzoate (b. p., see Example 1) in a 97% yield.

The ethyl acetate-pyridine mixture used as solvent in the above reaction may be replaced by other combinations of solvents, e.g. tetrahydrofuran-pyridine or abs. chloroform-pyridine in proportions between 1:9 and 9:1 without any substantial change in yield. When 4-methylpyridine is used as solvent in the above reaction the yield of isopropyl benzoate is 81%.

When the above reaction is performed in the absence of pTSA in any of the solvents mentioned above, the yield of isopropyl benzoate is reduced to below 40%.

EXAMPLE 7

To a mixture of 3-phenylpropionic acid (15.0 g) and isopropanol (6.61 g) in pyridine (30 ml) perchloric acid (0.150 g) and DCC (24.8 g) are added. After stirring at room temperature for 24 h acetic acid (10 ml) is added, and the reaction mixture is worked-up as described in Example 1 to give a 94% yield of isopropyl 3-phenylpropionate (b. p., see Example 2).

Perchloric acid may be replaced as catalyst in the above reaction by equimolar amounts of other strong acids, e.g. methanesulfonic acid, hydrogen chloride, nitric acid, hydrogen bromide, trifluoromethanesulfonic acid, hydrogen iodide, benzenesulfonic acid, or sulfuric acid, without any substantial change in yield.

If the above reaction is carried out in the absence of an acid catalyst the yield of isopropyl 3-phenylpropionate is 58%.

EXAMPLE 8

Using essentially the same reaction conditions as described in Example 3 esters were prepared from the alcohols and acids mentioned below with DCC as condensing agent and pyridine as solvent. The yields were in each case substantially higher when pTSA was used as a catalyst than when no strong acid was present in the reaction mixture. The following esters were made:

3-ester of estrone with acetic acid (20);
p-p¹-diester of diethylstilbestrol with propionic acid (20);
21-ester of dexamethasone with heptanoic acid (20);
21-ester of prednisone with 4-(bis(2-chloroethyl)amino)benzoic acid (14);
17β-ester of 19-nortestosterone with 3-phenylpropionic acid (20) and decanoic acid (20);
3-esters of 5-cholesten-3-ol and of 24-ethyl-5-cholesten-3-ol with 4-(bis(2-chloroethyl)amino)phenylacetic acid (21, 20);
17β-ester of 17β-hydroxy-1,4-androstadien-3-one with 10-undecenoic acid (20);
3,17β-diester of estradiol with 3-(4-(propyloxy)phenyl)propionic acid (15);
21-ester of 9α-fluoroprednisolone with acetic acid (20);
21-ester of hydrocortisone with 3-cyclopentylpropionic acid (20) and 4-(bis(2-chloroethyl)amino)phenylacetic acid (14);
17β-ester of testosterone with 3-(4-(butyloxy)phenyl)propionic acid (15), propionic acid (20), heptanoic acid (20);
21-ester of prednisolone with 3-(bis(2-chloroethyl)amino)phenylacetic acid (14), 4-(bis(2-chloroethyl)amino)phenylacetic acid (14), 2-acetamido-3-(4-bis(2-chloroethyl)amino)phenyl)propionic acid (14);
17β-ester of 17β-hydroxy-1-methyl-5α-androst-1-en-3-one with heptanoic acid (20);
21-ester of cortisone with 4-(bis(2-chloroethyl)amino)benzoic acid (14).

It is to be understood that the invention is not limited to the exact details of operation or exact compounds shown or described, as obvious modifications and equivalents will be apparent to one skilled in the art.

REFERENCES

1. Kurzer, F. and Douraghi-Zadeh, K. Chem. Rev. 67 (1967) 107.
2. Felder, E., Tiepolo, U., and Mengassini, A. J. Chromatogr. 82 (1973) 291.
3. Fieser, L. F. and Fieser, M. Reagents for Organic Synthesis, Wiley, New York 1967.
4. Zetzsche, F. and Fredrich, A. Ber. Deut. Chem. Ges. 72 (1939) 1735.
5. Vowinkel, E. Chem. Ber. 100 (1967) 16.
6. Henecka, H. in Müller, E. (Ed.) Methoden der organischen Chemie (Houben-Weyl), Band VIII (1952) 521.
7. Neelakantan, S., Padmasani, R., and Seshadri, T. R. Tetrahedon 21 (1965) 3531.
8. Fersht, A. R. and Jencks, W. P. J. Amer. Chem. Soc. 91 (1969) 2125.
9. Knoblich, J. M., Sugihara, J. M., and Yamazaki, T. J. Org. Chem. 36 (1971) 3407.
10. Hoffman, F. W. and Weiss, H. D. J. Amer. Chem. Soc. 79 (1957) 4759.
11. Cohen, S. G. J. Amer. Chem. Soc. 66 (1944) 1395.
12. Takahashi, S., Cohen, L. A., Miller, H. K., and Peake, E. G. J. Org. Chem. 36 (1971) 1205.
13. Poulsen, E. and Aldridge, W. N. Biochem. J. 90 (1964) 182.
14. Fex, H. J., Högberg, K. B., and Könyves, I. U.S. Pat. 3,732,260 (1973).
15. Diczfalusy, E., Fernö, O., Fex, H., and Högberg, B, Acta Chem. Scand. 17 (1963) 2536.
16. Könyves, I. and Liljekvist, J. (1975): In: Proceedings of the Sixth International Symposium on the Biological Characterization of Human Tumors, p. 98. Excerpta Medica, Amsterdam.
17. McOmie, J. F. W. Protective Groups in Organic Chemistry, Plenum Press, London 1973.
18. Djerassi, C. Steroid Reactions, Holden-day, San Francisco 1963, chapter 1.
19. Bell, R. P. The Proton in Chemistry, 2nd Ed., Chapman and Hall, London 1973, p. 26–28.
20. Negwer, M. Organisch-Chemische Arzeimittel and ihre Synonyma, Akademie-Verlag, Berlin, 1971.
21. Wall, M. E., Abernethy, Jr., G. S., Carrol, F. I. and Taylor, D. J. J. Med. Chem. 12 (1969) 810.
22. Bascombe, K. N. and Bell, R. P. J. Chem. Soc. (1959) 1104.

We claim:

1. In a process for the preparation of a steroid carboxylic acid ester of high purity and in improved yield, comprising reacting in solution a carboxylic acid, a steroid hydroxyl compound which has a cyclopentanophenanthrene carbon-carbon skeleton and contains up to a maximum of 40 carbon atoms and which is selected from the group consisting of steroid alcohols and phenols, and a carbodiimide, in the presence of pyridine or a 3- or 4- lower-alkylpyridine, the improvement which comprises the step of including in the reaction mixture a strong acid.

2. The process of claim 1, wherein the strong acid is employed in a catalytic amount.

3. The process of claim 2, wherein the amount of strong acid is in the range of 0.02 to 0.10 mole per mole of the limiting ester-forming component.

4. The process of claim 2, wherein the strong acid is sulfuric acid, nitric acid, perchloric acid, a sulfonic acid, or a hydrogen halide.

5. The process of claim 4, wherein the sulfonic acid is p-toluensulfonic acid or methane sulfonic acid.

6. The process of claim 4, wherein the hydrogen halide is hydrogen chloride, hydrogen bromide, or hydrogen iodide.

7. The process of claim 1, wherein the pyridine or lower-alkylpyridine is present in an amount at least equivalent to the limiting esterforming component.

8. The process of claim 7, wherein pyridine is employed.

9. The process of claim 1, wherein the carbodiimide is present in a molar amount at least equivalent to the molar amount of carboxylic groups.

10. The process of claim 9, wherein the carbodiimide is an N,N¹-dialiphatic or N,N¹-di-aromatic carbodiimide.

11. The process of claim 10, wherein the carbodiimide is N,N¹-dicyclohexylcarbodiimide.

12. The process of claim 1, wherein the reaction is performed in an inert solvent or a mixture of such solvents.

13. The process of claim 12, wherein the solent is selected from the group consisting of hydrocarbons, halogenated hydrocarbons, ethers, esters, and ketones.

14. The process of claim 13, wherein the solvent is selected from aliphatic ethers, esters, and ketones.

15. The process of claim 13, wherein the solvent is selected from chloroform, dichloromethane, benzene, chlorobenzene, and toluene.

16. The process of claim 14, wherein the solvent is selected from dioxane, tetrahydrofurane, diethylether, ethylacetate, and acetone.

17. The process of claim 1, wherein the reaction is performed at room temperature.

18. The process of claim 1, wherein the carboxylic acid and the hydroxyl compound are present in approximately equivalent amounts.

19. The process of claim 1, wherein the steroid hydroxyl compound is selected from the group consisting of primary and secondary alcohols and phenols.

20. The process of claim 1, wherein the carboxylic acid is a carboxylic acid having at most 22 carbon atoms, selected from the group consisting of aliphatic acids and phenylalkanoic acids.

21. The process of claim 1, wherein the carboxylic acid is a phenylalkanoic acid having a ring bis($\beta$- or $\alpha$-haloalkyl)amino group.

22. The process of claim 21, wherein said steroid contains at least one free hydroxy group in the 3-, 16-, 17-, or 21-positions, said positions being identified according to steroid nomenclature.

23. The process of claim 22, wherein the carboxylic acid is a phenylalkanoic acid having a ring bis($\beta$- or $\alpha$-haloalkyl)amino group.

24. The process of claim 1, wherein the strong acid has a thermodynamic dissociation constant K in water greater than one.

25. The process of claim 23, wherein said steroid hydroxyl compound is 19-nortestosterone or prednisolone.

* * * * *

UNITED STATES PATENT AND TRADEMARK OFFICE
CERTIFICATE OF CORRECTION

PATENT NO. : 4,181,669

DATED : January 1, 1980

INVENTOR(S) : Bertil Hansen and Krister Holmberg

It is certified that error appears in the above—identified patent and that said Letters Patent is hereby corrected as shown below:

Col. 4, line 68; ")" the close parenthesis mark should be on the line it is enclosing and not standing alone. No dashes are necessary except after the ")".

Col. 5, line 12; "primarily" should read -- primary --

Col. 6, line 8; "or" should read -- and --

Col. 9, lines 22, 36, 57 and 65; ")" the close parenthesis mark should be on the line it is enclosing and not standing alone. No dashes are necessary except after the ")".

Col. 9, lines 45 & 46; "-COCH$_2$OCO-)" should read -- -COCH$_2$OCO-) --

Col. 10, lines 10 & 11; "-COCH$_2$OCO-)" should read -- -COCH$_2$OCO- --

Col. 10, line 34; "2H, each" should read -- 2H each --

Col. 11, lines 21, 40 and 41; ")" the close parenthesis mark should be on the line it is enclosing and not standing alone. No dashes are necessary except after the ")".

Col. 12, line 3, Reference No. 10; "Hoffman" should read -- Hoffmann --

Col. 12, line 24, Reference No. 20; "Arzeimittel" should read -- Arzneimittel --

Signed and Sealed this

Eighth Day of July 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,181,669
DATED : January 1, 1980
INVENTOR(S) : Bertil Hansen and Krister Holmberg It is certified that error appears in the above—identified patent and that said Letters Patent is hereby corrected as shown below:

Col. 9, line 65; "11α,17-" should read -- 11β,17- --

Signed and Sealed this

Twelfth Day of August 1980

[SEAL]

Attest:

SIDNEY A. DIAMOND

*Attesting Officer*    *Commissioner of Patents and Trademarks*